United States Patent [19]

Lund et al.

[11] Patent Number: 4,467,117

[45] Date of Patent: Aug. 21, 1984

[54] PROCESS FOR THE PRODUCTION AND PURIFICATION OF 2,4,4'-TRICHLORO-2'-HYDROXYDIPHENYLETHER

[75] Inventors: Richard B. Lund, Jackson; Glenn W. Brown, Wagarville, both of Ala.

[73] Assignee: Ciba-Geigy Corporation, Ardsley, N.Y.

[21] Appl. No.: 464,532

[22] Filed: Feb. 7, 1983

[51] Int. Cl.$^3$ .............................................. C07C 41/26
[52] U.S. Cl. ................................................ 568/637
[58] Field of Search ........................................ 568/637

[56] References Cited

U.S. PATENT DOCUMENTS 3,506,720  4/1970  Model et al. .......................... 568/637

Primary Examiner—Bernard Helfin
Attorney, Agent, or Firm—Karl F. Jorda

[57] ABSTRACT

An improved synthesis of the bacteriostat 2,4,4'-trichloro-2'-hydroxydiphenylether is disclosed wherein the hydrolysis after diazotization is carried out at 175°–180° C. to increase the yield and reaction rate. The hydrolyzed product is distilled after neutralization to remove the major portion of undesirable colored products and phenolics. The distillate is then extracted with tetrachlorethylene to separate the product from non-phenolic by-products including the 25–28% 2,4,8-trichlorodibenzofuran which are present. The final product of the process then meets F.D.A. and commercial standards for use in soaps and cosmetics.

4 Claims, No Drawings

PROCESS FOR THE PRODUCTION AND PURIFICATION OF 2,4,4'-TRICHLORO-2'-HYDROXYDIPHENYLETHER

FIELD OF THE INVENTION

This invention relates to the synthesis of 2,4,4'-trichloro-2'-hydroxydiphenylether, a bacteriostat useful in the formulation of cosmetics and soaps. More particularly, this invention, in the synthesis of said 2,4,4'-trichloro-2'-hydroxydiphenylether by diazotization, relates more specifically to improved synthesis yields as well as more efficient removal of impurities arising from said synthesis.

BACKGROUND OF THE INVENTION

The bacteriostat 2,4,4'-trichloro-2'-hydroxydiphenylether covered by U.S. Pat. No. 3,506,720, is annually marketed in million-pound quantities under the trademark IRGASAN DP-300 ® for use in soaps and cosmetics. It has been produced from 2,4,4'-trichloro-2-aminodiphenylether(TADE) by diazotization and hydrolysis according to Equation 1:

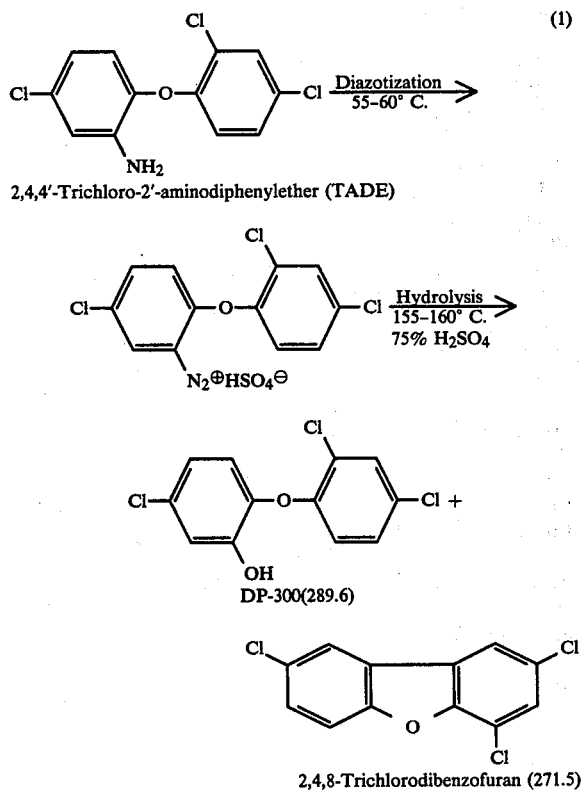

Products of this synthesis, in addition to the desired phenol (DP-300) obtained in 55% yield based on TADE, include 24–28% of 2,4,8-trichlorodibenzofuran (TCDBF) and traces of more than ten other compounds including phenolics and non-phenolics related to or derived from the furan compound.

Because of strict cosmetic industry and FDA specifications, the products of the above synthesis required extensive and intensive purification procedures including high-vacuum distillation, precipitation, filtration and solvent recrystallization leaving a yield (based on TADE) of about 53.5% IRGASAN DP-300.

The major compounds found as impurities in the synthesis according to Equation 1 and their concentration limits in the commercial product are as follows:

| | |
|---|---|
| 2,4-Dichlorophenol (2,4-DCP) | <0.01% |
| 4-Chlorophenol (4-CP) | <0.01% |
| 4,4-Dichloro-2-hydroxydiphenylether (DCHDPE) | <0.7% |
| 2,4,8-Trichlorodibenzofuran (TCDBF) | <10 ppm |
| 2,8-Dichlorodibenzofuran (DCDBF) | <1 ppm |

In the previous procedures these standards of purity were achieved by diazotizing molten 2,4,4'-trichloro-2'-aminodiphenylether with nitrosyl sulfuric acid at 55°–60° C. The diazotization reaction mass was hydrolyzed by 75% sulfuric acid at 155°–160° C. The organic phase was separated from the acid at about 120° C. The organic (upper) phase was adjusted to pH>12 with 50% caustic to form a slurry containing the water soluble sodium salt of IRGASAN DP-300 and precipitated furan (TCDBF). The slurry was filtered to remove most of the furan by-product. The alkaline filtrate was extracted with toluene to remove most of the associated non-phenolic impurities and then the product was acidified to form an oily lower organic phase containing the crude product and an aqueous phase containing some of the phenolic impurities. The organic phase was distilled, separating the fore run up to 180° C./1 mm from the main cut at 180°–225° C./1 m. The main cut of distilled IRGASAN DP-300 was recrystallized from an aliphatic petroleum solvent (Naphtholite 66/3) boiling in the range 130°–138° C. to yield a product meeting the above noted purity specifications. It is a slightly yellow crystalline material with a phenolic odor.

THE INVENTION

As a result of a review and study of the above noted previous procedures, it was found that the process for preparing and isolating 2,4,4'-trichloro-2'-hydroxydiphenylether is improved in yield, color and purity by the process of this invention. In addition, the prior process is greatly simplified and costly, time-consuming procedures are either avoided or condensed, resulting in a considerable savings in equipment and processing expenses.

The present invention comprises a process for the synthesis and purification of 2,4,4'-trichloro-2'-hydroxydiphenylether which comprises the steps of diazotizing 2,4,4'-trichloro-2-aminodiphenylether; hydrolyzing the resulting diazo compound by addition to $H_2SO_4$ (e.g. 75%) at a temperature range of about 175°–180° C.; separating the spent acid layer from the upper oily organic layer; distilling said oily organic layer, collecting the fraction distilling at 195°–197° C./4 mm; contacting said fraction with tetrachloroethylene; adjusting the tetrachloroethylene-fraction mixture with alkali hydroxide to pH 13 and agitating same; stopping agitation and separating the (top) aqueous layer from the heavier tetrachloroethylene layer containing the non-phenolic impurities including the 2,4,8-trichlorodibenzofuran; repeatedly extracting said aqueous product with at least 3 portions of tetrachloroethylene; neutralizing the so-extracted aqueous layer to pH 5–7; separating the resulting (bottom) product layer from the neutralized aqueous (top) layer and then recovering said 2,4,4'-trichloro-2'-hydroxydiphenylether in commercial purity.

DETAILED DESCRIPTION

In the previous processes, the diazotization reaction of Equation 1 above is carried out in a straightforward manner. The diazo compound in the past has been hydrolysed to convert it to desired hydroxy compound (among others) at temperatures in the range 155°–160° C.

We have found that if the hydrolysis is conducted at a temperature in the range 175°–180° C. the desired product 2,4,4'-trichloro-2'-hydroxydiphenylether (IRGASAN DP-300) is formed in greater amounts than at the lower temperature. Yield at this stage was increased from about 53–56% to 58–63%. The amount of furan impurity was also increased at this hydrolysis temperature. Experience with several hydrolysis runs indicates that the ratio of IRGASAN DP-300 to the furan was substantially constant at temperatures ranging from 135° to 180° C. (0.299–0.283).

It was discovered that by carrying out the hydrolysis of the diazonium salt of TADE at 175°–180° C. (instead of 155°–160° C.) that the yield improvement of about 5% was obtained and further, that kinetic studies showed the hydrolysis rate for the TADE diazonium salt to be more than six times as fast at 180° C. (compared to 160° C.). The total hydrolysis time including time for addition of reagents could be concluded within two hours. This was considerably less than the excess of 5 to 6 hours experience had dictated for the prior practice at 155°–160° C.

It was also discovered, in the course of studies of the prior process, that the crude hydrolysis product can be distilled immediately after the spent acid is removed without serious degeneration of the product. In fact, it was found that such a distillation provided a crude product with lower concentrations of undesirable phenols and of lesser color.

An advantage of the latter quality is that the lower color allows greater precision in splitting the phases during the step of subsequent extraction by tetrachlorethylene of the furan and other non-phenolic impurities.

After removal of the spent acid-phase, subsequent to hydrolysis, the crude mixture of IRGASAN DP-300 and furan impurity is adjusted to pH about 7 and vacuum distilled at 190°–198° C./4 mm. The resulting distillate is substantially colorless. The bulk of the furan and other non-phenolic impurities are then removed from the nearly colorless distillate by a polychlorinated lower aliphatic hydrocarbon or aromatic or chlorinated aromatic hydrocarbon solvent extraction. Experience has shown that three successive extractions will yield a product meeting legal and commercial purity standards but to ensure meeting such standards, five TCE extractions are preferred. After such a sequence, the product meets the specification limits noted above.

The residual solvent contained in the extracted product is then stripped by vacuum distillation at about 150° C./100 mm. followed by a vacuum steam stripping at 150° C. which removes any residual 2,4-dichlorophenol and 4-chlorophenol to below specification limits.

The residual molten product is then recovered either by crystallization in water or by hydroprilling.

Crystallization is carried out by the melt with about 2 parts (volumes) of water at 80° C. for one hour. The temperature was then dropped to 49° C. and stirred for 10–15 hours. Between 10–15 hours, the mixture goes from molten mass to a mushy mass of fine crystalline needles. These are too fine to filter but if the temperature is then dropped to room temperature (20°–28° C.) the crystals agglomerate in discrete bundles of 1–2 mm length. This mass is then filterable. The mass can be washed with water during filtration.

Hydroprilling is carried out by pumping the melt through capillaries into a 1% suspension of IRGASAN DP-300 crystals in water at 40°–42° C. Pellets of the product adhere to the crystal nuclei and are easily filtered and vacuum dried. The suspension water provides a solvent for any residual color and water soluble impurities.

As regards the hydrocarbon solvent, tetrachlorethylene ($Cl_2CH=CHCl_2$—TCE) is the preferred extractant but as it has low toxicity, low vapor pressure and a convenient boiling range, as mentioned above, other polychlorinated aliphatic hydrocarbons having 1 to 3 carbon atoms such as, methylene chloride, tetrachlorethane, ethylene dichloride, etc. as well as such aromatic hydrocarbon solvents as toluene, chlorotoluene, dichlorobenzene, etc. will serve as extractants for the non-phenolics. For best performance the solvent chosen should be immiscible with water, inert to sulfuric acid and sodium hydroxide and capable of dissolving the impurities formed.

The non-phenolic impurities have no commercial value nor are they easily converted to useful intermediates for further synthesis. Consequently, due to their toxicity they are incinerated. As TCE interferes with proper combustion of these materials, it is useful to distill off the TCE from these undesirable residues before incineration.

TCE boils at 120°–121° C. and is easily distilled and collected for recycling.

It should be noted that prior purification methods usually specified an expensive two-stage distillation of the final product before crystallization. This is expensive and requires subjecting the final product to temperatures approaching 180° C. At such temperatures there is a danger of significant amounts of impurities forming. As the commercial specifications require very low amounts of impurities, the present procedure which avoids such a late-stage heating is eminently desirable. As the distillation stage, which may form impurities takes place before the solvent extraction procedures which are very effective at removing these impurities, the final product easily meets these stringent specifications.

The invention will be more fully set forth in the appended example detailing the preferred procedure for carrying out this invention. While several equipment and reagent details and reaction conditions are set forth, art-recognized equivalents thereof may be substituted where they do not depart from the scope and intent of the invention as discussed above.

EXAMPLE

A two-liter 5-neck reactor, fitted with a bottom outlet stirrer, and addition ports, is charged with 147 ml of $H_2SO_4$ 96% and 168 ml nitrosylsulfuric acid 40%. The mixture is heated to 45°–50° C. An addition funnel 500 ml is charged with 210.6 ml of 2,4,4'-trichloro-2'-aminodiphenylether (TADE) 100% previously heated to 45°–50° C. and the TADE is added to the vigorously agitated reactor at a rate sufficient to maintain the mixture between 55°–60° C. Upon completion of the TADE addition, the heated mixture gives a negative starch/KI paper test. Additional nitrosylsulfuric acid (about 1 ml) is added until the starch/KI test is just positive. The reaction mass is cooled and 123 ml of water is added to the reaction mixture at a rate so that the exotherm does not heat the mixture to above about 60° C. Then the diluted mixture is agitated at 60° C. for about half an hour. The sulfuric acid content of this diazotization mass is about 50-55%.

A two-liter 3-necked reactor is charged with 39 ml water, 74 ml $H_2SO_4$ and 6-7 ml of tetrachlorethylene (TCE). The mixture is heated to 175°-180° C. Water is permitted to distil through the condenser so that this temperature can be maintained.

The diazotization mass is charged from the bottom outlet of the first reactor into the second hydrolysis-reactor over a two-hour period while the mixture is maintained at 175°-180° C. Upon completion of the addition the mixture is held until hydrolysis is complete by the negative diazo (R-salt) spot test. The TCE prevents clogging of the condenser. The completely hydrolyzed mixture is cooled to 120°-125° C. and the resultant layers are permitted to settle out. The top oily layer contains the desired material and is split by draining the bottom spent acid layer (554 ml) from the oily layer (215 ml). The desired oily layer is introduced into a one liter flask equipped for vacuum distillation. The acidic content of the flask is neutralized with NaOH solution 50% (about 0.5 ml). The TCE is removed at 150° C./100 mm and a 4-5% (10-12 ml) fore run, coming over at 190°-198° C./4 mm from a pot temperature of 203-204, is discarded. The lightly colored main distillation fraction (215-230 gm) is then distilled at 195°-197° C./4 mm from a pot temperature of 235°-240° C. into a liter reactor fitted with a bottom outlet.

To the distillate (216 ml) is added 216 ml TCE, 750 of water and 44 ml NaOH(50%) and the mixture is stirred and heated to 80° C. for 15 minutes. The agitation is stopped but the heating is continued at 80° C. until the phases separate (30 minutes). The bottom TCE/furan layer (267 ml) is split from (top) aqueous product layer.

Heating is discontinued and the aqueous product layer is extracted with five successive 120 ml portions of TCE. The separated TCE portions are combined with the first extract and separately distilled to recover the TCE for recycling. The residue of the furan and non-phenolics is incinerated. The agitated residual aqueous product layer is neutralized to pH 6-7 with about 24 gm $H_2SO_4$—96%. The resultant two phases are permitted to settle and the (bottom) product layer (180 fm) is split. The product is recovered by hydroprilling. Before hydroprilling the product is analyzed. The total yield of IRGASAN DP-300 based on TADE is 60-61% (depending on assay method) and exceed the FDA purity specification.

As can be seen, this process provides at least a 5% increase in yield of high purity product and effects considerable savings by eliminating an expensive distillation step, and labor intensive furan precipitation and filtration steps. In addition, by replacing the final molecular distillation with an earlier non-critical distillation followed by repeated aqueous and organic extractions, the possible formation of deleterious non-phenolics and other impurities is relegated to those process sequences where these products can be easily removed and eliminated from the final product.

What is claimed is:

1. A process for the synthesis and purification of 2,4,4'-trichloro-2'-hydroxydiphenylether which comprises the steps of diazotizing 2,4,4'-trichloro-2'-aminodiphenylether; hydrolyzing the resultant diazo compound by addition to $H_2SO_4$ at a temperature range of about 175°-180° C.; separating the spent acid layer from the upper oily organic layer; distilling said oily organic layer, collecting the fraction distilling at 195°-197° C./4 mm; contacting said fraction with a polychlorinated lower aliphatic hydrocarbon solvent of 3 or less carbon atoms or an aromatic or chlorinated aromatic hydrocarbon solvent; adjusting the solvent-fraction mixture with alkali hydroxide to pH 13 and agitating same; stopping agitation and separating the (top) aqueous product layer from the heavier solvent layer containing the impurities; repeatedly extracting said aqueous product with at least 3 portions of solvent; neutralizing the so-extracted aqueous layer to pH 6-7; separating the resulting (bottom) product layer from the neutralized aqueous layer and then recovering said 2,4,4'-trichloro-2'-hydroxydiphenylether in commercial purity by hydroprilling or crystallization and filtration.

2. The process according to claim 1 wherein said polychlorinated lower hydrocarbon solvent is tetrachlorethylene.

3. The process according to claim 2 wherein the furan and non-phenolic impurities are completely removed by five tetrachlorethylene extractions.

4. The process according to claim 1 wherein the recovery of the pure 2,4,4'-trichloro-2'-hydroxydiphenylether is carried out by hydroprilling of the molten product into an aqueous suspension of the crystallized product.

* * * * *